(12) United States Patent
Peters

(10) Patent No.: US 9,187,335 B2
(45) Date of Patent: Nov. 17, 2015

(54) PULSE JET WATER DESALINATION AND PURIFICATION

(75) Inventor: Bruce H. Peters, Colorado Springs, CO (US)

(73) Assignee: Altmerge, LLC, Colorado Springs, CO (US)

(*) Notice: Subject to any disclaimer, the term of this patent is extended or adjusted under 35 U.S.C. 154(b) by 283 days.

(21) Appl. No.: 13/595,887

(22) Filed: Aug. 27, 2012

(65) Prior Publication Data
US 2012/0321528 A1 Dec. 20, 2012

Related U.S. Application Data

(63) Continuation-in-part of application No. 13/445,751, filed on Apr. 12, 2012, which is a continuation-in-part of application No. 13/221,814, filed on Aug. 30, 2011, now Pat. No. 8,721,980.

(60) Provisional application No. 61/469,233, filed on Mar. 30, 2011.

(51) Int. Cl.
*B01J 19/00* (2006.01)
*B01J 19/24* (2006.01)
(Continued)

(52) U.S. Cl.
CPC ............... *C01C 1/04* (2013.01); *B01J 19/241* (2013.01); *B01J 19/26* (2013.01); *C01B 3/386* (2013.01);
(Continued)

(58) Field of Classification Search
CPC .... B01J 19/00; B01J 19/0013; B01J 19/0053; B01J 19/20; B01J 19/24; B01J 19/26; B01J 7/00; B01J 4/00; B01J 4/002; B01J 2219/00; B01J 2219/00157; B01J 12/00; B01J 8/00; B01J 8/0285; B01J 8/0496; B01J 2208/00; B01J 2208/00752; B01J 2208/00902; B01J 8/02; B01J 8/04; C02F 1/26; C02F 1/265; C02F 1/46; C02F 1/4604; C02F 2103/08

USPC .......... 422/129, 187, 198; 423/351, 352, 385, 423/387, 396, 398, 400
See application file for complete search history.

(56) References Cited

U.S. PATENT DOCUMENTS

| 3,297,777 A | 1/1967 | Grantom et al. |
| 3,694,770 A | 9/1972 | Burwell et al. |

(Continued)

FOREIGN PATENT DOCUMENTS

| JP | 59038514 | 3/1984 |
| KR | 2009-071939 A | 7/2009 |

(Continued)

OTHER PUBLICATIONS

Machine translation of KR 2009071939 A, Application No. KR 1020070139882, which was published Jul. 2, 2009.

(Continued)

*Primary Examiner* — Natasha Young
(74) *Attorney, Agent, or Firm* — Trenner Law Firm, LLC; Mark D. Trenner

(57) ABSTRACT

A pulse jet system and method is disclosed. In an example, the pulse jet system includes a combustion chamber, intake ports to deliver combustion agents to the combustion chamber, an expansion chamber to cool a combustion product following combustion of the combustion agents in the combustion chamber, and an exhaust to exit the cooled gas from the expansion chamber. In another example, the pulse jet system includes a combustion chamber with intake ports to deliver combustion agents to the combustion chamber, wherein the combustion chamber is part of a four cycle engine. The pulse jet system also includes an expansion chamber to cool a combustion product following combustion of the combustion agents in the combustion chamber.

5 Claims, 9 Drawing Sheets

(51) Int. Cl.

| | | |
|---|---|---|
| *C01C 1/04* | (2006.01) | |
| *C01B 17/04* | (2006.01) | |
| *C01B 17/74* | (2006.01) | |
| *C01F 11/38* | (2006.01) | |
| *C01F 11/40* | (2006.01) | |
| *C07D 251/60* | (2006.01) | |
| *C07C 45/00* | (2006.01) | |
| *C07C 45/38* | (2006.01) | |
| *C01B 21/30* | (2006.01) | |
| *C01B 21/32* | (2006.01) | |
| *C01B 3/38* | (2006.01) | |
| *C01B 3/48* | (2006.01) | |
| *C01C 1/18* | (2006.01) | |
| *B01J 19/26* | (2006.01) | |
| *C02F 1/04* | (2006.01) | |
| *F23C 15/00* | (2006.01) | |
| *F23G 7/00* | (2006.01) | |
| *C01B 31/18* | (2006.01) | |
| *C01B 31/20* | (2006.01) | |
| *B01J 19/20* | (2006.01) | |
| *B01J 4/00* | (2006.01) | |
| *B01J 12/00* | (2006.01) | |
| *B01J 8/00* | (2006.01) | |
| *B01J 8/02* | (2006.01) | |
| *B01J 8/04* | (2006.01) | |
| *C02F 1/26* | (2006.01) | |
| *C02F 1/06* | (2006.01) | |

(52) U.S. Cl.
CPC . *C01B 3/48* (2013.01); *C01B 17/04* (2013.01); *C01B 17/74* (2013.01); *C01B 21/30* (2013.01); *C01B 21/32* (2013.01); *C01B 31/18* (2013.01); *C01B 31/20* (2013.01); *C01C 1/18* (2013.01); *C01F 11/38* (2013.01); *C01F 11/40* (2013.01); *C02F 1/04* (2013.01); *C07C 45/002* (2013.01); *C07C 45/38* (2013.01); *C07D 251/60* (2013.01); *F23C 15/00* (2013.01); *F23G 7/00* (2013.01); *B01J 2219/0013* (2013.01); *B01J 2219/00123* (2013.01); *C01B 2203/0261* (2013.01); *C01B 2203/0283* (2013.01); *C01B 2203/061* (2013.01); *C01B 2203/1058* (2013.01); *C02F 1/06* (2013.01); *Y02W 10/37* (2015.05)

(56) References Cited

U.S. PATENT DOCUMENTS

| | | | |
|---|---|---|---|
| 4,185,559 A | 1/1980 | Little | |
| 4,186,058 A | 1/1980 | Katz et al. | |
| 4,294,812 A | 10/1981 | Oler | |
| 4,304,308 A | 12/1981 | Munding et al. | |
| 4,433,540 A | 2/1984 | Cornelius et al. | |
| 4,580,504 A * | 4/1986 | Beardmore et al. | 110/261 |
| 4,595,459 A * | 6/1986 | Kusakawa et al. | 202/177 |
| 4,697,358 A | 10/1987 | Kitchen | |
| 4,886,444 A | 12/1989 | Hirase et al. | |
| 5,188,806 A | 2/1993 | Kuehner et al. | |
| 5,279,260 A | 1/1994 | Munday | |
| 5,797,737 A | 8/1998 | Le Gal et al. | |
| 5,925,223 A | 7/1999 | Simpson et al. | |
| 5,932,074 A | 8/1999 | Hoiss | |
| 6,003,301 A * | 12/1999 | Bratkovich et al. | 60/204 |
| 6,146,693 A | 11/2000 | Chernyshov et al. | |
| 6,398,125 B1 | 6/2002 | Liu et al. | |
| 6,460,342 B1 | 10/2002 | Nalim | |
| 6,722,295 B2 | 4/2004 | Zauderer | |
| 7,097,675 B2 | 8/2006 | Detering et al. | |
| 7,225,620 B2 | 6/2007 | Klausner et al. | |
| 7,241,522 B2 | 7/2007 | Moulthrop et al. | |
| 7,354,561 B2 | 4/2008 | Kong | |
| 8,043,479 B2 | 10/2011 | Duesel, Jr. et al. | |
| 8,721,980 B2 * | 5/2014 | Peters | 422/187 |
| 2002/0117125 A1 | 8/2002 | McMaster et al. | |
| 2002/0151604 A1 | 10/2002 | Detering et al. | |
| 2003/0021746 A1 | 1/2003 | Fincke et al. | |
| 2004/0219400 A1* | 11/2004 | Al-Hallaj et al. | 429/13 |
| 2005/0097819 A1 | 5/2005 | Lomax, Jr. et al. | |
| 2005/0103643 A1 | 5/2005 | Shoup | |
| 2005/0109604 A1 | 5/2005 | Zlotopolski | |
| 2006/0083671 A1 | 4/2006 | Obayashi et al. | |
| 2007/0051611 A1 | 3/2007 | Rives et al. | |
| 2007/0072027 A1 | 3/2007 | Sridhar et al. | |
| 2007/0128477 A1 | 6/2007 | Calhoon | |
| 2007/0193870 A1 | 8/2007 | Prueitt | |
| 2008/0141974 A1 | 6/2008 | Bechtel | |
| 2010/0126876 A1 | 5/2010 | Peters | |
| 2010/0154429 A1 | 6/2010 | Peters | |
| 2010/0187128 A1 | 7/2010 | Neubert et al. | |
| 2010/0224477 A1 | 9/2010 | Peters | |
| 2011/0024283 A1 | 2/2011 | Peters | |
| 2011/0047962 A1 | 3/2011 | Kenyon et al. | |
| 2011/0126511 A1 | 6/2011 | Glaser et al. | |
| 2011/0174605 A1 | 7/2011 | Ugolin | |
| 2012/0252999 A1* | 10/2012 | Peters | 526/340 |
| 2013/0161007 A1 | 6/2013 | Wolfe et al. | |
| 2014/0134057 A1* | 5/2014 | Peters | 422/138 |

FOREIGN PATENT DOCUMENTS

| | | |
|---|---|---|
| KR | 10-2007-0139882 | 11/2009 |
| WO | 94-23186 A1 | 10/1994 |

OTHER PUBLICATIONS

English Abstract of KR 2009071939 A, which was previously published as KR 1020070139882 and discloses the relationship and which was published Jul. 2, 2009.

International Search Report and Written Opinion for Int. Appl. No. PCT/US2011/049793, mailed Apr. 25, 2012, 9 pp.

Chao, R.E., "Thermochemical Water Decomposition Processes", Industrial and Engineering Chemistry Product Research Development, 1974, p. 94-101.

Nishida, M., "Effect of Electronic Excitation on Laser Heating of a Stationary Plasma", 1982, J. Phys. D: Appl. Phys., 15, 1951-1954.

International Search Report and Written Opinion for PCT/US2012/052562 dated Jan. 23, 2013, 10 pp.

International Search Report and Written Opinion dated Oct. 30, 2012 for PCT/US2012/033369, 10 pp.

International Search Report and Written Opinion dated Sep. 23, 2014 for International Application No. PCT/US2014/040627, 13 pp.

\* cited by examiner

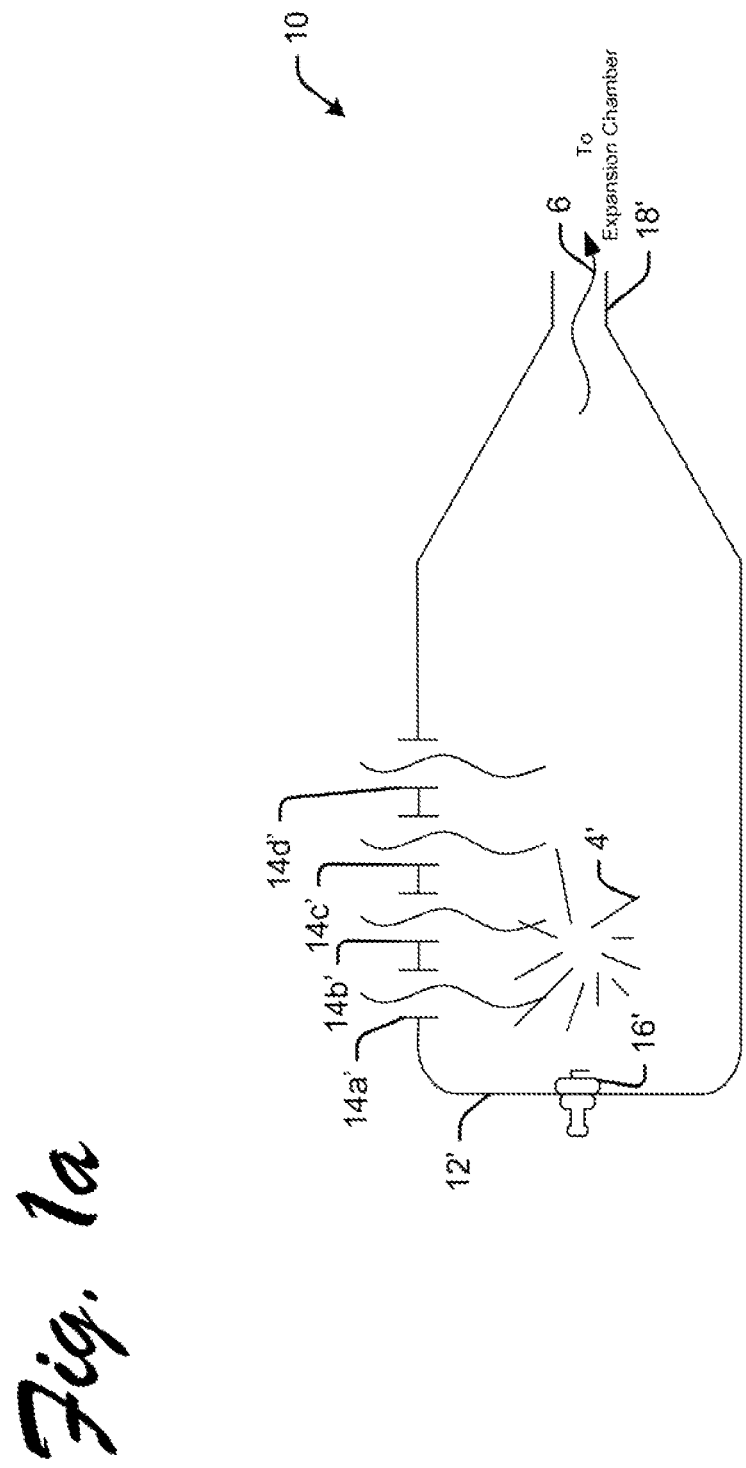

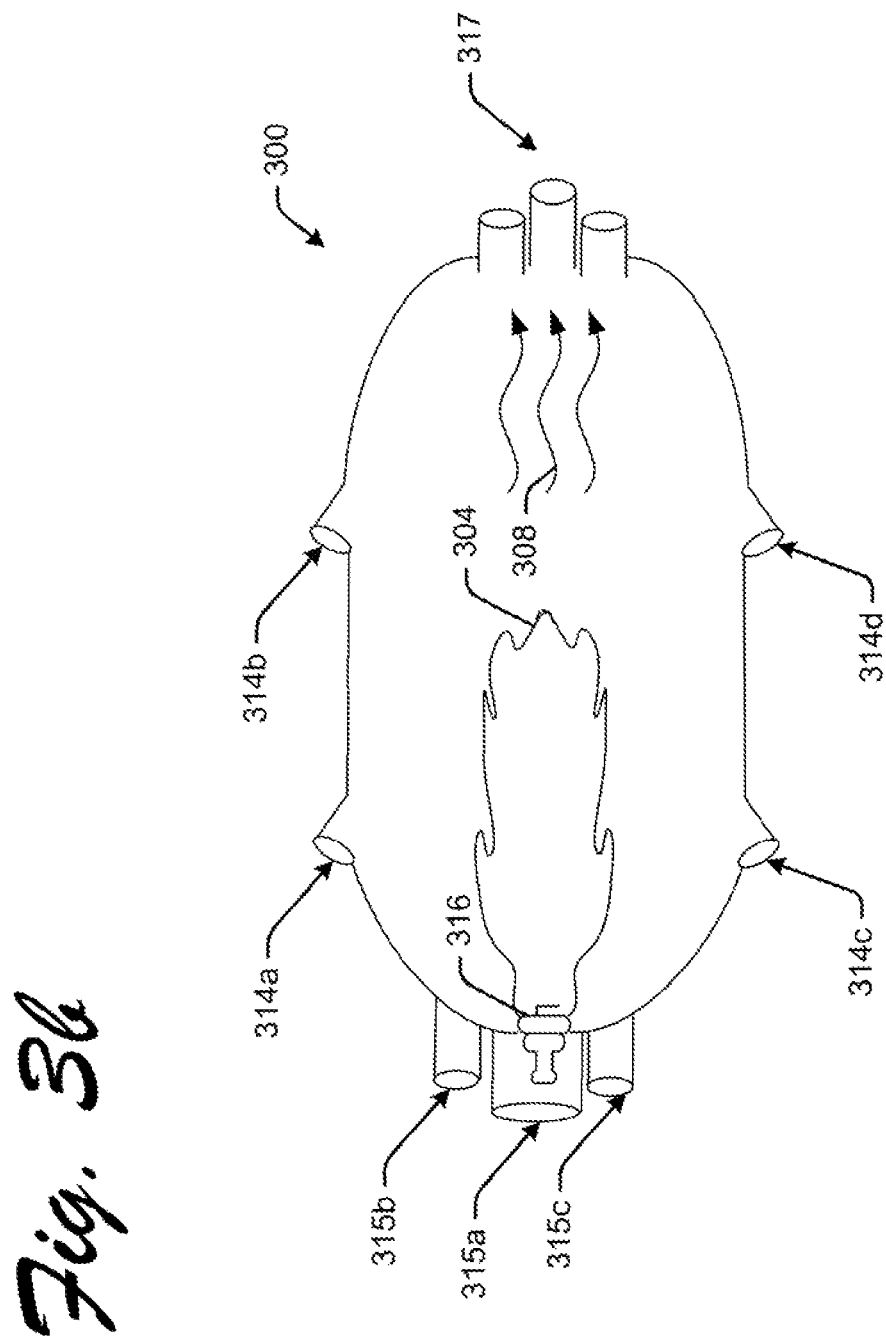

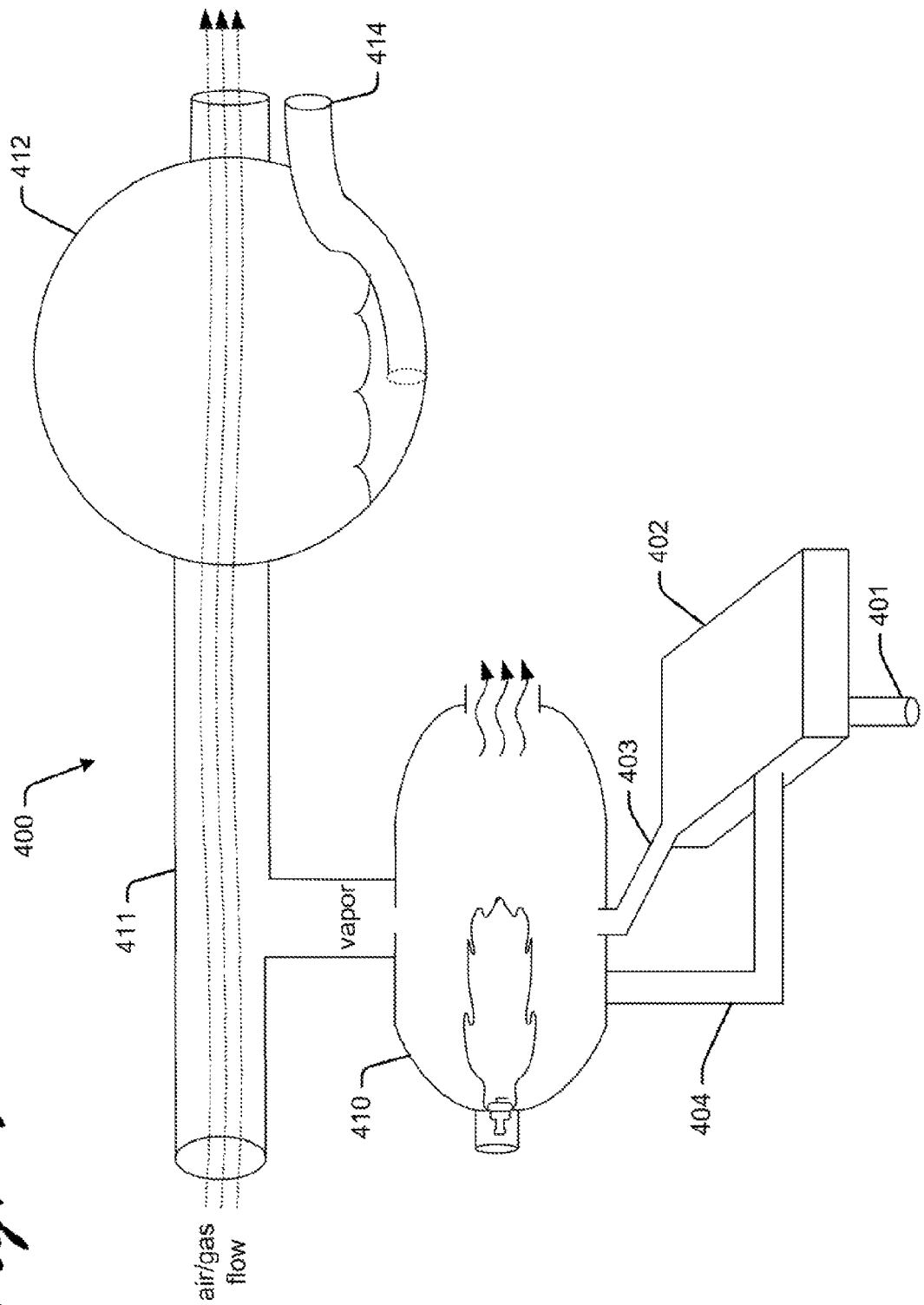

PULSE JET WATER DESALINATION AND PURIFICATION

PRIORITY CLAIM

This application is a continuation-in-part of U.S. patent application Ser. No. 13/445,751 (corresponding to PCT/U32012/033369) filed Apr. 12, 2012 and titled "Production of chemical compounds" of Bruce H. Peters, which is a continuation-in-part of U.S. patent application Ser. No. 13/221,314 (corresponding to PCT/US2011/049793) filed Aug. 30, 2011 now U.S. Pat. No. 8,721,980 and titled "Systems and methods of producing chemical compounds" of Bruce H. Peters, which claims priority to U.S. Provisional Patent Application No. 61/469,233 filed Mar. 30, 2011 and titled "Device and process for underground rock fracturing and heating and nitrate and hydrocarbon formation using a hydrogen powered pulse jet" of Bruce H. Peters, each of which is hereby incorporated by reference in entirety as though fully set forth herein.

BACKGROUND

Chemical production techniques are often complex, requiring large installations or facilities, e.g., as factories. These chemical production facilities often emit a wide range of pollutants and thus are heavily regulated. In addition, the chemical production equipment often is specifically configured to product a particular chemical composition. Any change in the chemical composition often requires that the chemical production equipment be reconfigured, which can be costly and time consuming, both undesirable qualities at a large chemical production facility.

BRIEF DESCRIPTION OF THE DRAWINGS

FIG. 1a shows an alternative intake chamber for the pulse jet system.

FIGS. 3a-b show other example configurations of the pulse jet system for chemical production.

FIG. 4 shows another example configurations of the pulse jet system for water desalination.

DETAILED DESCRIPTION

Figure 1:
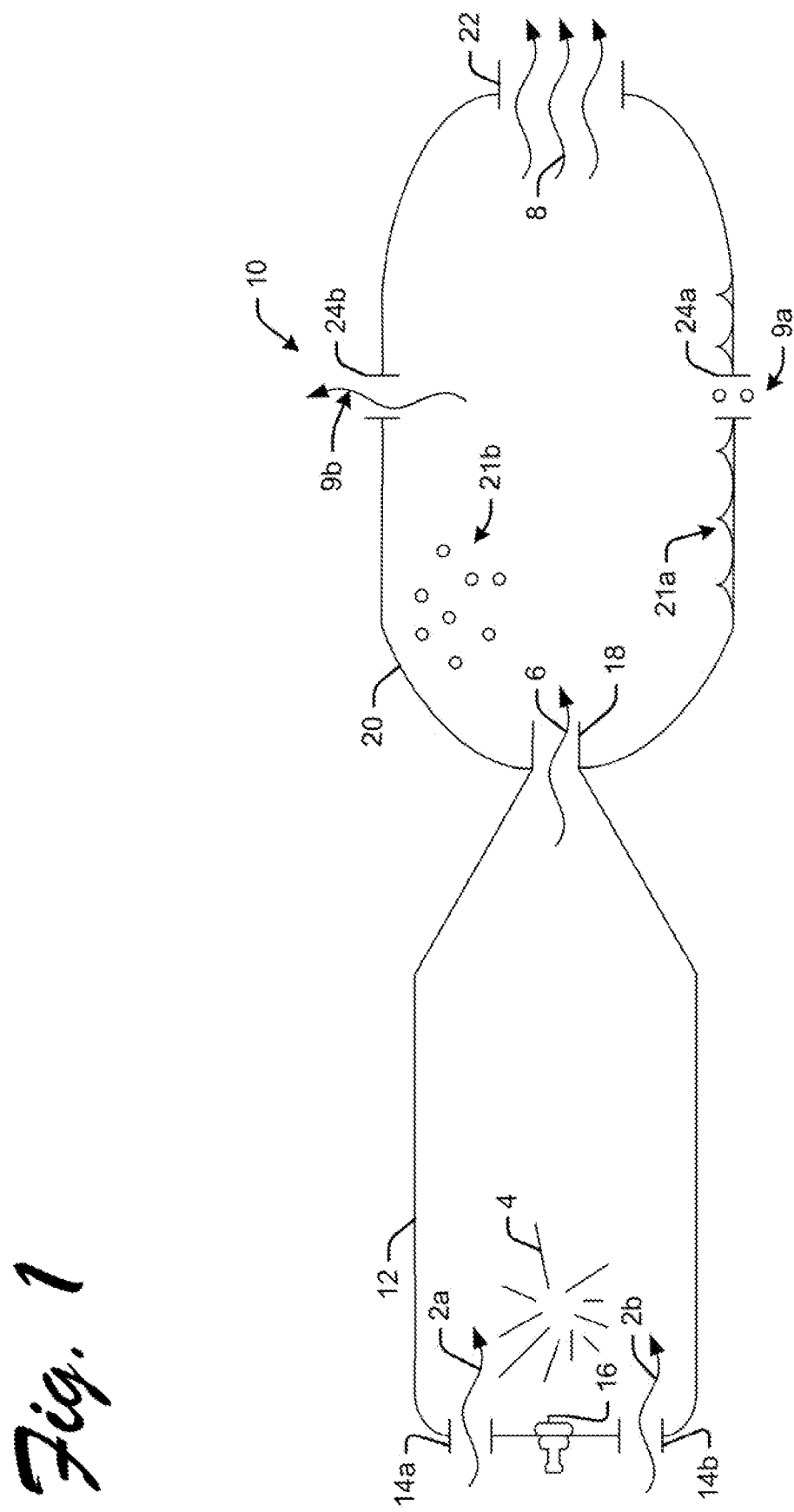
FIG. 1 shows an example pulse jet system.

A pulse jet system and method are disclosed. The pulse jet system may be used, for example but not limited to, reforming methane, $CH_4$, and other hydrocarbons into hydrogen; as a device used for drilling into, tunneling into, fracturing and/or heating subterranean structures; a device used for mining and a method to process recovered ores through differential centrifugation and metal recovery by liquification at different melting points; as a process for admitting H2 or other combustibles, with oxygen or ambient air, outside an underground combustion chamber to improve efficiency. It is noted that the pulse jet system and method may use hydrogen to ignite ammonia (or other difficult to ignite combustibles), e.g., for the purpose of using these materials in chemical production and/or in propulsion. In addition, a method is disclosed for adding water vapor into the pressurized exhaust of the pulse jet and expanding this into an unpressurized chamber, e.g., for the purpose of water purification, desalination, and/or for cooling (e.g., refrigeration and air conditioning). In an example implementation, the pulse jet system and method may be embodied in a modified 4 cycle engine for producing ammonia.

In an example, systems and methods are disclosed for producing nitrogen compounds, which can then be used to produce inorganic fertilizers, among other uses. Inorganic fertilizers can be synthesized using nitrogen to produce ammonia, nitrite and nitrate-based fertilizers to enhance crop yields and quality. The systems and methods also produce focused explosive force, pressure, and heat, which can be used to drill into and fracture structures in the earth's subsurface. Example applications include, but are not limited to, aiding with oil and gas recovery and drilling operations. These and other products and applications will be understood by those having ordinary skill in the art after becoming familiar with the teachings herein.

An example pulse jet system includes an intake chamber having intake ports for entry of a gas mixture. An igniter ignites the gas mixture in the intake chamber. A nozzle restricts exit of the ignited gas mixture from the intake chamber. An expansion chamber cools the ignited gas with a cooling agent. The expansion chamber has an exhaust where the cooled gas exits the expansion chamber. There may also be an exit port to remove products in aqueous and/or liquid form. A chemical compound product is formed in the expansion chamber.

An example method includes: igniting a gas mixture in an intake chamber, restricting exit of the ignited gas mixture from the intake chamber to increase temperature and pressure, cooling the ignited gas in an expansion chamber, and collecting a chemical compound product from the expansion chamber.

In an example, ammonia is ignited by adding hydrogen as a source of energy (e.g., a combustant) in the pulse jet, and used in a 4 cycle engine process. The use of hydrogen combined with ammonia as a combustant can also be used in the exhaust of a drilling machine to provide a propelling force. For example, the pulse jet can be used as part of an underground drilling or fracking device, wherein uncombusted hydrogen, oxygen, air and/or hydrocarbon can be directed into the rock strata forward of the combustion chamber so that this can infiltrate into the rock strata and detonate to add to the power of the device to tunnel (rack. For example, a pipe may be added at the front of the device that carries hydrogen, oxygen. The device can use hydrogen and/or oxygen to initiate combustion, and thus make easier combustion of the ammonia or $N_2O$ or $CH_4$, which are also used as combustants. Thus, the pulse jet can be used as a propelling device when hydrogen with oxygen are detonated at any of a wide range of concentrations, along with ammonia or nitrous oxide, which are otherwise difficult to ignite and ignite over a much smaller range of concentrations.

In another example, a hydrocarbon (alone and/or with hydrogen) can be used as the combustive agent, along with oxygen or air in making certain chemicals. For example, natural gas (e.g.: methane) can be used as a combustant: along with a 1/10 hydrogen to each 9110 $CH_4$ (with hydrogen admitted at the site of ignition). The combustion of $CH_4$ is intermixed with water saturated ambient air and also produced ammonia, $NH_4OH$ and aqueous $NH_4NO_3$ in a manner similar to using hydrogen alone as a combustive agent. In actual application, with the addition of one part carbon dioxide to each 3 parts of ambient air, urea was produced. In this application, black particles of carbon and exhaust carrying combusted hydrocarbons were also produced.

Before continuing, it is noted that as used herein, the terms "includes" and "including" mean, but is not limited to, "includes" or "including" and "includes at least" or "including at least." The term "based on" means "based on" and "based at least in part on." It is further noted that the figures illustrate high level diagrams, including cross-sectional schematics of the components described herein, for purposes of illustration and simplicity. It will be readily appreciated by those having ordinary skill in the art from the accompanying description that the components are implemented as described in enclosures (e.g., a chamber), even when "true" cross-sectional views, three dimensional views, or perspective views are not provided.

FIG. 1 shows an example pulse jet system 10. The drawings are shown as simple schematic diagrams, but it should be appreciated that one having ordinary skill in the art will understand the construction of the system using readily available components and manufacturing techniques, based on these schematics and corresponding description herein. Other configurations of systems and devices for carrying out the operations of the chemical processes are also possible.

The example pulse jet system 10 is shown in FIG. 1 including a combustion chamber or intake chamber 12. The intake chamber 12 may be configured with a number of inlet or intake ports 14a-b for entry of a gas mixture (illustrated by gas flow 2a and gas flow 2b).

Although two intake ports 14a-b are shown in a back wall of the intake chamber 12 in FIG. 1 for purposes of illustration, it is noted that any suitable number of port(s) and/or port configuration may be provided and positioned based on design considerations.

Design considerations for determining the number, sizing, and positioning of ports may include, but are not limited to the number and type of gas or gases being introduced to the intake chamber 12, timing of the introduction of gas or gases, flow rates, pressure, and other parameters.

For purposes of illustration, FIG. 1a shows another example intake chamber 12' having four intake ports 14a' through 14d' along an upper sidewall of the intake chamber 12'. In this example, port 14a' may supply hydrogen gas, port 14b' may supply oxygen, port 14c' may supply ambient air, and port 14d' may supply water, water vapor/steam or other gas directly to the intake chamber 12'. It is noted that in FIG. 1a the prime (s) designation is used to refer to like components (as shown in FIG. 1), and may not be described separately for FIG. 1a.

The process allows for production of a variety of products, depending on the amounts and ratio of gases combusted and the temperatures and pressures achieved, which can be further controlled by varying the amount of water vapor (which acts as a cooling and modulating agent) entering the intake chamber. In this way, both ammonia ($NH_3$) and nitric acid ($HNO_3$) are made in ratios reflecting the gases admitted to the system, and the temperature and pressures chosen. Nitric acid is made through the following formula:

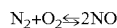
$$N_2 + O_2 \leftrightarrows 2NO$$

And then

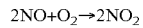
$$2NO + O_2 \rightarrow 2NO_2$$

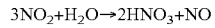
$$3NO_2 + H_2O \rightarrow 2HNO_3 + NO$$

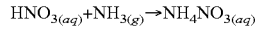
$$HNO_{3(aq)} + NH_{3(g)} \rightarrow NH_4NO_{3(aq)}$$

In this example, the direct injection of water or water vapor/steam into the intake chamber 12' begins a cooling process, and absorption of nitric oxide into a nitrogen dioxide phase, before the ignited gas exits the intake chamber 12'. This configuration has been shown to favor production of ammonia at high conversion efficiencies. This configuration also results in production of an ammonia liquor fertilizer product (instead of ammonium nitrate produced using the intake chamber 12 in FIG. 1). The process can be further facilitated by adding a catalyst, such as magnetite or ruthenium, to the intake chamber 12'.

With reference again to FIG. 1, an igniter 16 is provided. The igniter 16 may be positioned to ignite the gas mixture within the intake chamber 12, as illustrated by explosion 4. The specific number and positioning of the igniter 16 may also vary based on design considerations, such as those set forth above. For example, a backup igniter may be provided.

Ignition of the gas mixture 2 causes a high temperature, high pressure explosion 4 within the intake chamber 14. Accordingly, the intake chamber 12 may be configured in such a manner so as to safely accommodate many, repeated explosions over time, without weakening the walls of the intake chamber 12. Indeed, it is found that the pressure within the chamber may be kept low for safety considerations, as the bulk of the chemical reactions occur focused within the very high temperature and pressure of the limited area of explosion within the chamber.

In an example, the intake chamber 12 tapers toward an end opposite the intake ports 14a-b. A nozzle 18 may be provided on the tapered end of the intake chamber 12. The nozzle 18 forms an outlet from the intake chamber 12, and serves as an inlet to an expansion chamber 20. A seal (not shown) may be provided between the intake chamber 12 and the expansion chamber 20. Such a configuration restricts exit of the ignited gas 6 flowing in from the intake chamber 12, thereby increasing temperature and/or pressure in the intake chamber 12 for a more efficient conversion process.

The expansion chamber 20 serves to cool the ignited gas 6 flowing into the expansion chamber 20. In an example, a cooling agent may be provided in the expansion chamber 20. The cooling agent may be water (illustrated by reference 21a), water vapor (e.g., a mist or water vapor illustrated by reference 21b), or a combination thereof. Other cooling agents may also be used and are not limited to water-based cooling agents.

The expansion chamber 20 has an exhaust 22 where the cooled gas 8 exits the expansion chamber 20. During cooling, a chemical compound product is formed in the expansion chamber 20. The chemical compound product can be collected in solid or aqueous form 9a at a collection port 24a and/or in gas form 9b at a collection port 24b. Chemical compound product is referred to generally herein by reference number 9. Again, the desired number and positioning of exhaust 22 and collection port 24 may be based at least in part on design considerations.

Figure 1B:
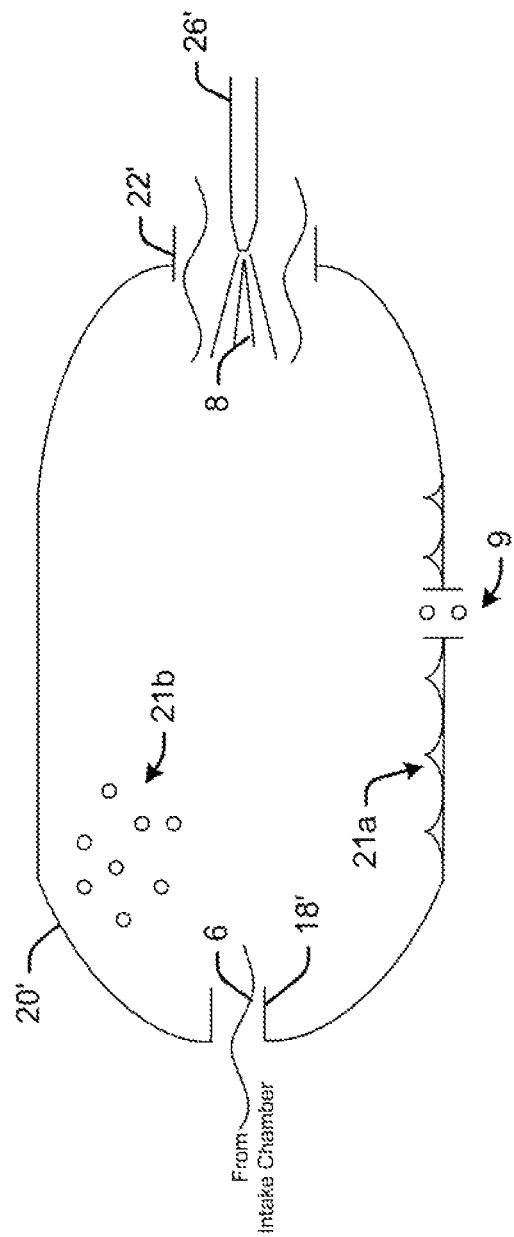
FIG. 1b shows an alternative expansion chamber for the pulse jet system.

For purposes of illustration, FIG. 1b shows another example expansion chamber 20'. In this example, the expansion chamber 20' includes an injection port 26' which enables the direct injection of a supplemental cooling agent 21c into the expansion chamber 20'. For example, the injection port 26' can be used to controllably inject a fine mist or vapor of water into the expansion chamber 20'. The cooling agent 21c injected by the injection port 26 may be used as a substitute for the cooling agent already in the expansion chamber 20', or in addition to the cooling agent(s) 21a and/or 21b already provided in the expansion chamber 20'. In any event, direct injection facilitates rapid cooling, of the gas 6 entering the expansion chamber 20'.

Although one injection port 26' is shown at the exhaust 22', any number and/or position of injection port(s) 26' may be provided, again based on design considerations.

It is noted that the specific materials used, and sizing of each component, may vary at least to some extent based on design considerations, desired mode of operation (see, e.g., example use cases below), and desired output product and quantity of the product. Appropriate safety precautions should also be observed due to the temperatures, pressures and explosive nature of the reactions.

In an example, the chambers may be manufactured of stainless steel. Nozzles, inlets, and outlets, may be manufactured of suitable metal materials. Unidirectional nozzles may be utilized, and gaskets and seals may also be provided, as appropriate, in order to ensure that the proper temperature and pressures can be maintained for accomplishing the reactions.

It will be appreciated that the pulse jet system 10 may be used to make any of a wide variety of chemical compounds. For example, the chemical compound product may be ammonia liquor, ammonium nitrate, nitric acid, and other chemical combinations of nitrogen with hydrogen and/or oxygen.

Before continuing, it should be noted that the examples described above are provided for purposes of illustration, and are not intended to be limiting. In an example, the components and connections depicted in the figures may be used. Other devices and/or device configurations may also be utilized to carry out the operations described herein.

During use of the pulse jet system 10, example operations may include igniting a gas mixture in an intake chamber, restricting exit of the ignited gas mixture from the intake chamber to increase temperature and pressure, cooling the ignited gas in an expansion chamber, and collecting a chemical compound product from the expansion chamber. The operations may be repeated at a rapid pace so as to be substantially continuous in nature, and/or to form a concentrated chemical compound product.

In an example, when used to produce nitrates. The reaction includes the explosion-producing nitrates in the intake chamber 12. The nitrates formed by the explosion are vented into the expansion chamber 20 containing steam or cold mist. In addition, water vapor in the ambient air (with or without using additional oxygen or nitrogen and/or with or without a catalyst) may also facilitate an environment of high heat and pressure. The temperature and pressure cause the nitrates to form ammonia and nitrogen oxide, which when quickly cooled in water, forms nitrogen dioxide. The nitrogen dioxide can combine with the water to form nitric acid, which combines with the ammonia to produce ammonium nitrate and nitrite in aqueous solution.

In another example, if a carbon-based gas (e.g., carbon monoxide or carbon dioxide) is used instead of a nitrogen-based gas, methane and more complex hydrocarbons can be produced abiotically. It is noted that the terms "explosion" and "combustion" are used interchangeably. Detonation may also occur in some applications (e.g., fracturing and drilling).

In another example, admitting into the explosive chamber an excess of hydrogen in relation to oxygen for combustion, along with carbon dioxide and, with restriction of admitted nitrogen, results in methane production. The amount of carbon admitted as carbon dioxide results in a production of methane at high efficiency and up to about 90% of admitted carbon is converted to methane.

The operations shown and described herein are provided to illustrate example implementations. It is noted that the operations are not limited to the ordering shown. Still other operations may also be implemented. It is also noted, that various of the operations described herein may be automated or partially automated.

Further operations may include redirecting gas (e.g., nitric oxide) from the expansion chamber 20 to the intake chamber 12 to reduce presence of the gas in the exhaust. Further operations may also include various mechanisms for injecting the cooling agent. For example, water may be injected directly into the ignited gas 6 as the gas 6 enters the expansion chamber 20. Introducing water may be at an angle about 180 degrees to the ignited gas 6 entering the expansion chamber 20. Still further operations may include injecting a cooling agent directly into the intake chamber 12 (e.g., as shown in FIG. 1a) to begin cooling in the intake chamber 12. Beginning cooling in the intake chamber 12 has been shown to facilitate absorption of nitric oxide and converting the nitric oxide to a nitrogen dioxide phase to favor high-efficiency ammonia production. Yet further operations may also include adding a catalyst to the intake chamber 12. Yet further operations may include high efficiency ammonium nitrate production.

The pulse jet system 10 may be used to in any of a wide variety of different ways. The following use cases illustrate some examples for using the pulse jet system 10.

In an example use case, the pulse jet system 10 may be used for a new method of performing high pressure and/or high temperature industrial chemical production. Examples are production of polyethylenes from alkanes, and coal gas reformation, as well as any other chemical reaction under pressure and not adversely affected by the presence of hydrogen, oxygen, and water, each of which are present in the processes described herein utilizing a hydrogen/oxygen pulse jet.

In another example use case, the pulse jet system 10 may be used for production of methane gas and/or other higher order hydrocarbons. When carbon dioxide is added to the intake chamber 12 in molar proportion to hydrogen and oxygen, the unburned hydrogen combines with carbon to produce higher order hydrocarbon(s).

In another example use case, the pulse jet system 10 can be used to cool gases by admitting a fluid and/or vapor with KCL, and/or other potassium, and/or phosphorus compounds. Such supplemental cooling agents can be introduced directly into the intake chamber 12 and/or the expansion chamber 20. Accordingly, the chemical compound product which is formed may be a so-called "complete" fertilizer (i.e., containing each of the essential nutrients: nitrogen, phosphorus, and potassium). The fertilizer can be manufactured as part of a continuous product.

In another example use case, the pulse jet system 10 may be used to recover ammonia as a gas. In addition to ammonia in aqueous solution. In such an example, the expansion chamber may be modified to include both a fluid collection port (for collecting liquid chemical compound product) and a gas collection port (for collecting gaseous chemical compound product).

In another example use case, the pulse jet system 10 may be used with calcium carbonate (e.g., limestone) and/or other lime-based product. During use, the nitrogenous oxides combine with the calcium carbonate to directly form a calcium nitrate chemical compound product.

In another example use case, the pulse jet system 10 may be operated with multiple passes, whereby the product (where the product is a gas) is reintroduced into the intake chamber. Such an example enables the chemical compound product to be concentrated.

In another example use case, the pulse jet system 10 may be operated to produce supercritical water (e.g., water of about 374° C. and higher). The supercritical water formed by this process can be used in other chemical production processes and/or other commercial uses.

Indeed, not all of the uses need to be directed to making a chemical compound product. That is, although a chemical compound product may be formed during the process, the desired end-result may be something other than the production of the chemical compound product. In such use-cases, the chemical compound product may be considered a "byproduct" of the reaction. The following use cases illustrate some of these alternatives for using the pulse jet system 10 for various applications.

In an example use case, the gas mixture is a hydrogen pulse jet and, can be used to produce electromagnetic pulses. It has been found that the explosion in the intake chamber causes radios to fail for between about 2 to 3 seconds after each pulse. Accordingly, the pulse jet system 10 may have application for disabling radio communications, disabling improvised explosive devices (IEDs), and/or assisting in testing electrical equipment that is sensitive to radio communications.

In another example use case, the pulse jet system 10 may be used as a pulse jet system for fracturing subsurface structures. Such pulse jet systems may have application, for purposes of illustration, in the oil and gas exploration and/or production fields.

Figure 2A:
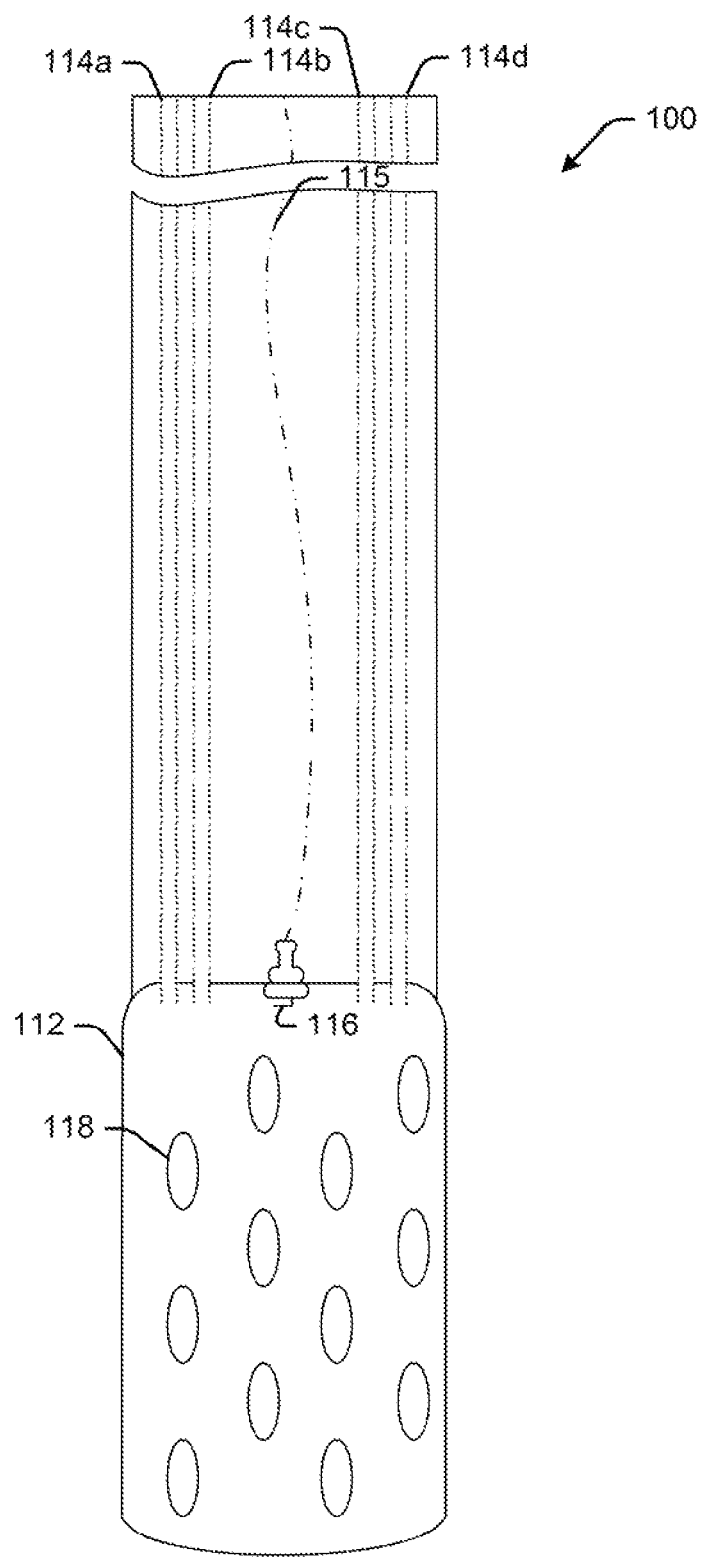
FIGS. 2ac show other example configurations of the pulse jet system for heating, fracturing, and/or drilling subsurface structures.
Figure 2B:
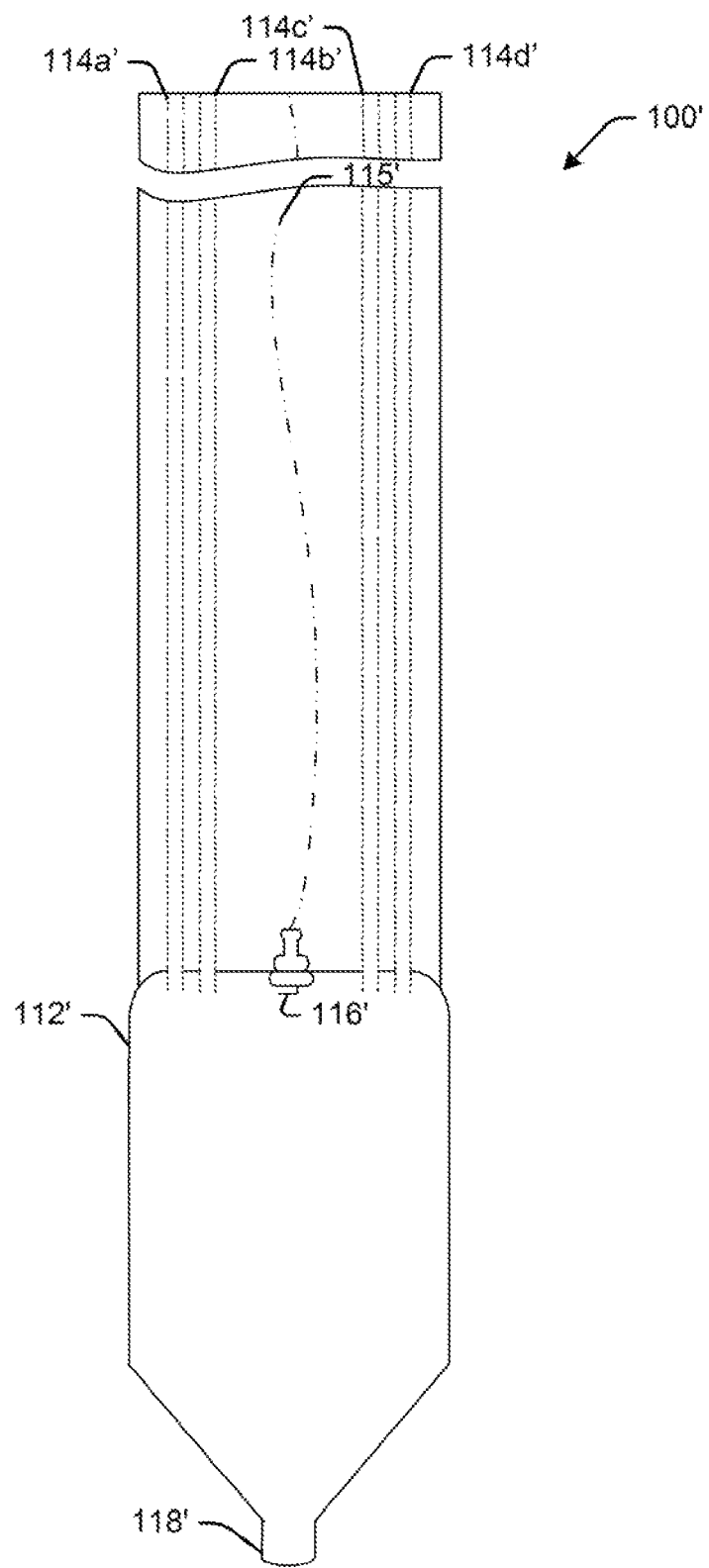
Figure 2C:
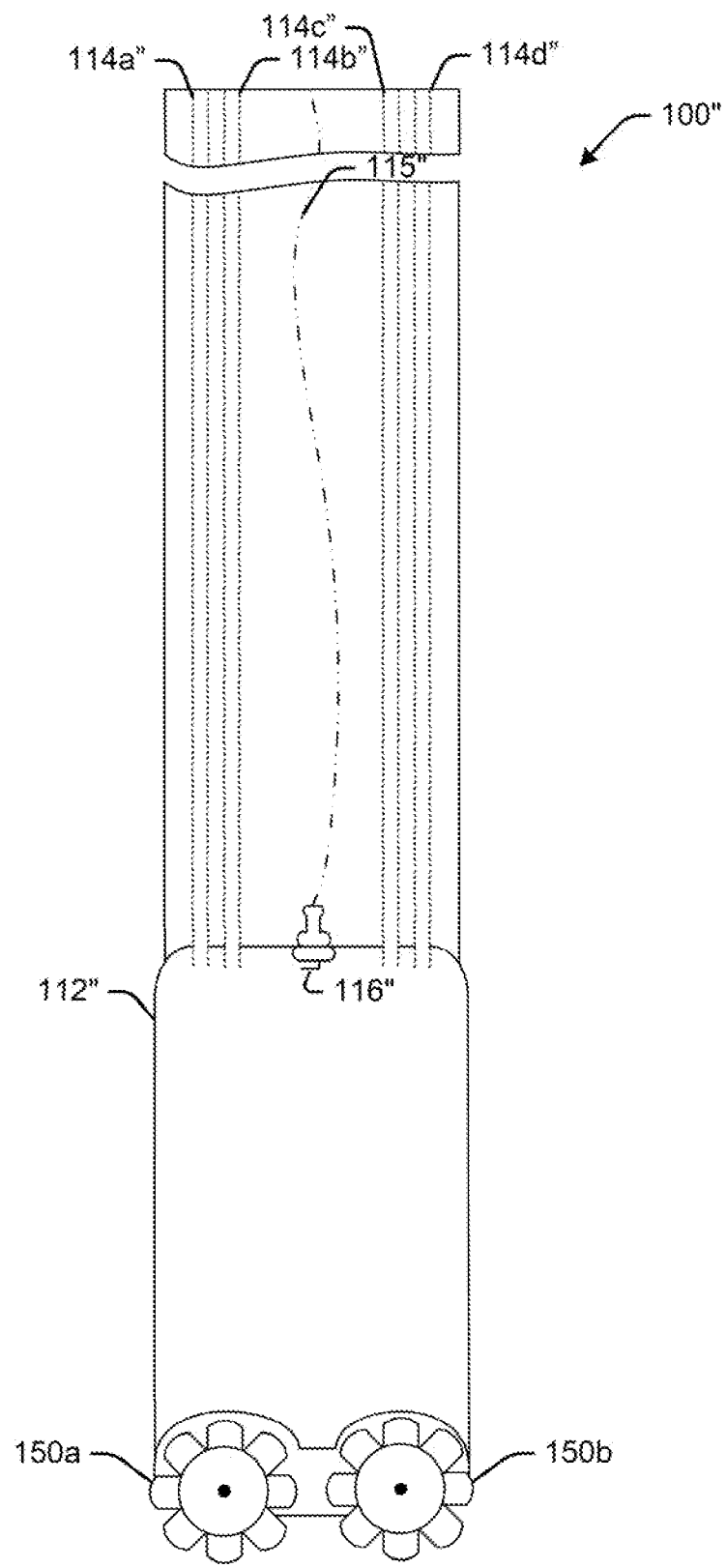

FIGS. 2a-c show example modifications of the pulse jet system described above with reference to FIG. 1, as it may be used as a pulse jet system 100. The pulse jet system 100 may be used, e.g., for heating, fracturing, and/or drilling subsurface structures. In these use cases, the pulse jet system described above with reference to FIG. 1 has been modified such that the expansion chamber is no longer used. It is noted, however, that the expansion chamber, or other chamber, may be used based on the particular end-use or application.

In an example use case, the pulse jet system 100 includes a combustion chamber 112, which can be provided at the end of a drilling rig. Tubing 114a-d may be provided through a well casing of the drilling rig, so that the appropriate gas (gases), gas mixture(s), and/or cooling agent(s) can be provided at the earth's surface even when the combustion chamber 112 is located in the earth's subsurface. Electrical wiring 115 may also be provided for the igniter 116. In another example, a remote or wireless connection may be implemented to activate the igniter 116. Or the igniter 116 may be activated automatically, e.g., using a timer.

During operation, the gas flow, cooling agent flow, and spark timing can all be controlled from the surface, and can vary based on the application and desired results. The sizing of the combustion chamber 112 can vary, as can the size and number of openings 118 through which the explosive force exits the combustion chamber.

The high temperature, high pressure reaction described above with reference to FIG. 1 may be produced in the combustion chamber 112. The process causes explosions, triggered by the internal sparking device. The exploded gas produces controlled blast(s) of high pressure and steam (i.e., the product of oxygen and hydrogen burning). The use of water pumped into the combustion chamber may be used to cool the chamber and also results in further steam production.

However, instead of the explosion causing the gas to exit into an expansion chamber (as described above with reference to FIG. 1), the explosion causes the gas to exit through one or more openings 118 formed in the combustion chamber 112.

Accordingly, the force of the controlled explosion can be used for drilling operations in the earth's subsurface. By way of illustration, the gases may include hydrogen and oxygen, $CH_4$, and/or other hydrocarbons, which react in the combustion chamber 112 to produce high pressure steam. As such, the byproduct is water and can generally be safely discharged into the surrounding environment.

FIG. 2a includes a perforated chamber having multiple openings 118 so that the force of the explosion causes fracturing of the surrounding subsurface structures. Other configurations of the combustion chamber 112 are also contemplated. For example, FIG. 2b shows another configuration, wherein the combustion chamber 112' includes a single opening 118' is provided at the end of a pointed drill head to direct the force of the explosion in a predetermined direction (e.g., downward). FIG. 2c shows yet another configuration, wherein the combustion chamber 112" includes rotary drill bit(s) 150a-b. The force of the explosion in the combustion chamber 112" can be directed past a drive mechanism to cause rotating of the drill bits 150a-b, and thus used for drilling operations. The examples shown in FIGS. 2a-c are shown only for purposes of illustration. Still other examples are also contemplated.

It is noted that the pressure and shock produced during the process may result in fractures to the surrounding rock and subsurface structures. The heat produced may also cause tar in the underground sand structures to become more liquid and thereby enable better extraction.

It should be understood that the operations utilize hydrogen, oxygen and/or an ambient air powered pulse jet to produce heat, pressure, and shock. When placed underground, the result is fracturing and heating underground, potentially petroleum-bearing strata, to aid in petroleum recovery in an environmentally friendly manner (e.g., producing water as a byproduct). The explosive force may also be used to drill into and fracture underground structures and thereby aid in petroleum recovery and/or other drilling applications.

The pulse jet system and method has been described as it may be used for propulsion, and/or to ignite ammonia which can be used as a fuel in the pulse jet system used for propulsion or an ICE. In addition to being an alternative form of energy production, the pulse jet system and method has also been described herein as it may be used for the production of chemicals. Further embodiments will now be described.

In an example, the pulse jet system and method may be used as a fracturing device to inject hydrogen with or without ambient air with or without adding oxygen, outside of the chamber and ignition device and directly into the underground rock or structure. This combination of hydrogen and oxidizer expands and infiltrates into the underground structures, and its explosive combustion may loosen and pulverize the subsurface or other material through which it passes. The combustion then occurs in a widespread area into which the hydrogen and oxygen (or hydrocarbon and oxygen) have infiltrated, resulting in a more powerful combustion than occurs when the combustion is limited to being enclosed within a combustion chamber. This results in a higher pressure over a more widespread subsurface region than occurs with hydraulic fracturing and uses less water and no or less other chemicals used in hydraulic fracturing.

In an example, the pulse jet system and method may be used to enclose and encapsulate an iron chamber in a steel case so that it can be replaced if needed.

In an example, the pulse jet system and method may be used for tunneling, and specifically for mining underground minerals and processing over into concentrated metallic products. In this application, a combustion chamber including an ignition device(s) is connected to a source of hydrogen or gaseous hydrocarbon (or combination thereof), and to oxygen and/or ambient air, with or without water vapor, and is configured so that gases from combustion or detonation is directed, e.g., via a system of valves and exhaust ports, to propel the devices forward (and to direct rearward gases and steam under pressure to force rearward fractured and pulverized subterranean materials through which the device has parsed) while producing pulse like combustion/detonations. Other ports and nozzles directed toward the part of the device (or at various angles) are fitted with valves allowing the energy to be directed to propel the unit forward and the fractured material backward and/or to direct explosions/combustion product (e.g., gas, steam, water vapor) to loosen, modify, pulverize or otherwise reform subterranean materials.

The pulse jet system and method may be of large diameter to enable tunneling, or of smaller diameter to facilitate being directed (e.g., by wire or wireless contact with controllers above ground, the result of being operated robotically by programming) along a seam of ore or other region. Thus in application to mining, the pulse jet system may be implemented as a device directed along a seam or region of concentrated ore which is pulverized and atomized and forced rearward and collected for processing. In an example method, the ore may be subjected to high speed centrifugation while suspended in air, water, or chemical and detergents, which augment the process. The particles are collected according to weight and size so that some separation of the various ores in a seam (or lead) occurs. Examples are ores common to the Rocky Mountain region, which contain Au, Ag, Cu, Zn, tin, etc. in dose approximation. These particles are then subjected to high temperatures and the various metals collected at the specific temperatures at which these liquefy.

The pulse jet system and method may also be used as commercially suitable degrees of metallic separation. For example, the pulse jet system may be connected to a rapidly rotating drum centrifuge or other separator. Finely ground ore may be added to the separator, and ore particles collect and concentrate according to size and weight. The largest and heaviest particles are separated at the lowest rotating speed. The smallest and lightest (e.g., copper, zinc, etc.) concentrate and collect at the more rapid speeds. The separated particles are then heated progressively (e.g., by heat generated and exhausted from the combustion chamber) above their respective melting points, and the liquid metals are separated and collected.

The current mining technique of removing the ore along with large quantities of non-ore-containing surrounding rock (and associated separation, e.g., using cyanide) can be avoided. The pulse jet system and method also avoids dust generation, and the need for large quantities of water for processing the discharge of toxic and/or radioactive dust and uranium or cyanides. This also reduces the cost of meeting regulations on ore processing, which have previously prevented legal mining in small claims and mines.

It is noted that hydrogen and other combustibles, along with oxygen and/or ambient air, may also be discharged into the structures outside of, but to the front or side of, the combustion chamber, propelling itself through mineral formations and discharging reformed and pulverized material to the rear, for further processing.

It is also noted that the pulse jet system and method may be used in in propulsion. In an example, hydrogen (because of its ability to ignite at concentrations between 4 and 73%) can be used to ignite hydrocarbons or ammonia (which itself is difficult to ignite) that may be injected into or in front of the hydrogen frame front. Water as vapor or fine spray, can also be injected. This can further increase the mass of material exhausted at the rear nozzle of the device increasing its efficiency for use in propulsion. The admission of hydrogen to create a flame front into which ammonia is admitted as in a modification of use in a standard 4 cycle internal combustion engine. This allows ignition of ammonia at levels of compression below those used in modified Diesel engines which may use ammonia as fuel.

As described above, it is also noted that the pulse jet system and method, may be used in the production of chemicals using elevated, temperatures. For example, the pulse jet system and method may be used for production of urea and other carbon-containing chemicals using hydrocarbons as combustibles. By way of illustration, the pulse jet system may be embodied as a 4 cycle internal combustion engine which makes production of ammonia and other ammonia based chemicals possible.

In processes wherein the production of carbon, CO, and carbon dioxide or other carbon containing combustion products aides the chemical process by providing a substrate. An example is the production of urea in a single step. In this process, a hydrocarbon (e.g. propane, although other gases such as methane or ethane, or vaporized liquid petroleum products such as gasoline can also be used) is introduced into the combustion chamber along with ambient air, carbon dioxide, and water vapor.

In an actual example run, products including urea and particles of carbon and other gaseous inflammable products (e.g., lighter weight than propane and air) burned with a steady blue flame, showing that the gas produced in the process was similar or identical to natural gas. In addition, the liquid recovered included urea, $NH_2CONH_2$, in aqueous solution, and was easily separable from the solid carbon. Reformed liquid and gaseous hydrocarbons were also produced.

In producing urea, as well as other more complex hydrocarbons and nitrogen containing hydrocarbons, carbon in the form of carbon monoxide and carbon dioxide combine with ammonia according to the equation:

$$2NH_3+CO_2 \rightarrow NH_2COO^-NH_4^+ \rightarrow NH_2CONH_2+H_2O$$

Unlike chemical processes wherein the presence of carbon may contaminate the product, production using hydrocarbons in the pulse jet system (e.g., all gaseous petroleum, liquefied petroleum as a vapor or mist, or various alcohols and other combustible gases or liquid hydrocarbons, ammonia, hydrogen, various combinations to be used as both reactant substrates and/or agents of combustion) for the multiple chemical reactions achieved through selecting the combination and balance of fuels and reactants and water vapor needed to optimize the production of desired product, and eliminate or minimize less desirable products or byproducts.

The hydrocarbons may combust with ambient air and/or oxygen in various combinations. Hydrogen can be added to the combustive mix in any amount. In combustive processes for chemical manufacture using the pulse jet system, chemical admitted into the reaction chamber and not consumed by combustion remain to act as reactants. The combustion creates a frame front in the combustion chamber that varies in temperature, pressure, chemical content, and water content, as it advances toward the exhaust nozzle. At the flame front, various chemical radicals form and interact and recombine, forming the desired products.

Figure 3A:
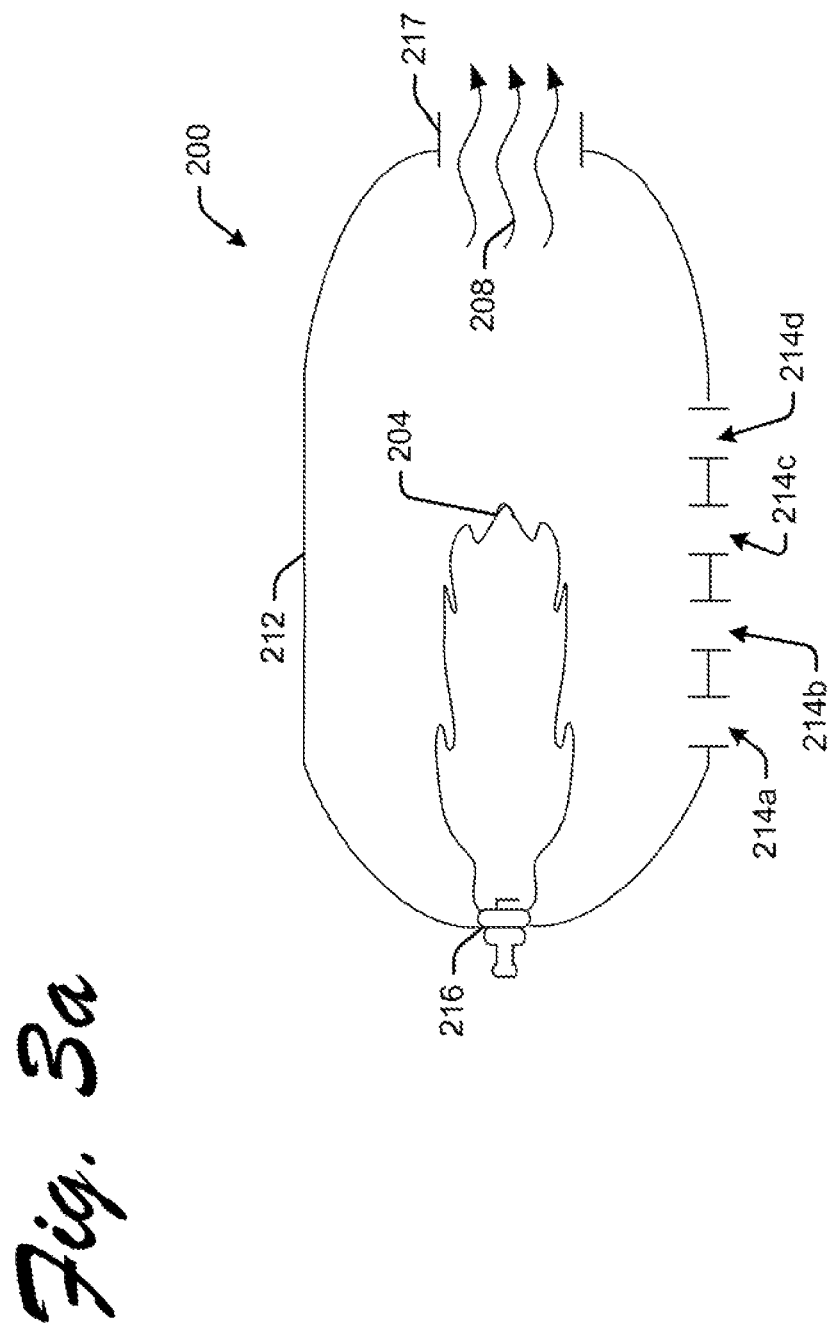

FIGS. 3a-b show other example configurations of the pulse jet system for chemical production. In FIG. 3a shows an example pulse jet system 200. The example pulse jet system 200 includes a combustion chamber 212. Although not shown, the combustion chamber 212 (and 312 in FIG. 3b) may be connected downstream to an expansion chamber or other outlet (e.g., collection means or secondary processing chamber). It is also noted that the combustion chamber 212/312 may be utilized in series and/or in parallel with other combustion chambers. The combustion chamber 212/312 is shown for purposes of illustration of example configurations but is not intended to be limiting in any way.

The combustion chamber 212 may be configured with a number of inlet or intake ports 214a-d for entry of gases. Although four intake ports 214a-d arranged as a single array are shown for purposes of illustration, it is noted that the number of port(s) and/or port configuration may be varied and positioned based on design considerations, as discussed above. For purposes of illustration, FIG. 3b shows another example combustion chamber 312 having four intake ports 314a-d having a different configuration.

In an example, port A (e.g., 214a or 314a) may supply hydrocarbon gas, port 14b' may supply carbon dioxide and/or water vapor, port 14c' may supply ambient air and/or oxygen, and port 14d' may supply water as vapor/steam/mist. All reactants may be admitted serially at or just beyond the front of the flame to enhance the process. The ports may include tubing (e.g., to the respective gas canisters) and may be configured as one-way valves into the combustion chamber.

In an example, the pulse jet system 200/300 shown in FIGS. 3a-b may be implemented as 4 cycle engine in a power stroke (third stroke) with injectors for hydrogen or other combustible, along with water vapor into the intake and with separate injectors located to admit materials into the cylinder beyond the flame front (flame 204/304 produced by igniter 216/316 in FIG. 3a-b, respectively) and into and beyond the exhaust valve. The pulse jet system 200/300 can also be used with hydrocarbon fuel. It is noted that all reactants may be admitted serially, at, or just beyond the flame front to enhance the process.

The process allows for production of a variety of products (gaseous, liquid, and/or solid), for example as illustrated by effluent 208/308 from the combustion chamber 212/312, depending on the amounts and ratio of gases combusted and the temperatures and pressures achieved. The figures illustrate example use of the pulse jet system 200/300 with methane as a combustible and substrate, along with added carbon dioxide (e.g., via an entry port 214/314). The result of combustion and ambient air with water mist or vapor (and added hydrogen and/or oxygen as desired) in the production of urea.

The reactants may be added to the combustion chamber 212/312 via ports 214a-d/314a-d (and/or separate inlets 315a-c in FIG. 3b). The reactants can be added serially, at or immediately beyond the flame front, as it moves toward the exit. Water vapor as mist, vapor, spray, or steam, may also be admitted beyond (distal to) the flame front, where the water serves to dissolve, absorb, or interact with the produced chemical. This results in the aqueous solution and also serves as a source of cooling for the combustion chamber.

In using the pulse jet system 200/300 with only hydrogen, oxygen (with or without nitrogen) and carbon dioxide, gaseous and liquid products which combust are separable from excessive hydrogen remaining uncombustible after combustion. Thus, hydrocarbons, both gaseous and liquid, are able to be formed by the process abiotically. This finding supports the conclusion that natural hydrocarbons may be, at least partially formed from substrate chemicals at high pressure and temperature, deep beneath the earth's surface. Thus, natural petroleum products may be formed in other ways than the biotic production of "fossil" fuels.

In another example, the pulse jet system 200/300 and method may be implemented in a 4 cycle internal combustion engine, modified as described herein, to use hydrogen as the primary combustible, specifically admits ambient air dense with water vapor into the combustion chamber, and employs injectors just beyond the flame front during the third cycle of the 4 cycle process. Thus, during the combustion process, reactants (various combinations of water vapor/mist, ambient air, oxygen, carbon dioxide, etc.) are injected just in front of the flame front 204/304 during a power producing phase, and may be injected at or just beyond the exhaust valve(s) 217/317. In this way, ammonia, ammonium nitrate, urea, and other chemicals can be made according to the proportions of combustibles, reactants, and water vapor. The product is collected in aqueous solution and the exhaust gas collected, discharged or further treated as desired.

In another example, the pulse jet system 200/300 and method may be implemented in a 4 cycle internal combustion engine, modified as described herein, for production of methanol (e.g., wood alcohol) and other alcohols including ethanol, ethyl alcohol, and methanol, among other products. Methanol may be produced using the pulse jet process to produce synthesis gas to convert methane, natural gas, propane, or other low molecular weight hydrocarbons into synthetic gas as per the following equations:

$$CH_4+H_2\rightarrow CO+3H_2$$

and $$CO+H_2O\rightarrow CO_2+H_2$$

$$CH_3H_8+3H_2O\rightarrow 3CO+7H_2$$

and $$3CO+3H_2O\rightarrow 3CO_2+3H_2$$

In this process, the pulse jet system 200/300 may be employed as both the reforming furnace and shift converter. The hydrocarbon feed stock is heated and desulfurized and subjected to NaOH scrubbing to remove organo-sulfurs. This now pure gas hydrocarbon is admitted to the combustion chamber 212/312 where a combustion occurs at about 760-980° C. (producing a pressure of about 600 psi with nickel catalyst, with or without potassium oxide) by modifying the combustion with water vapor. Ambient air or oxygen can be added to the system to keep the temperature high. The nitrogen of the air reacts in ammonia synthesis. More steam, resulting from heat produced during the process, is added and the mixture enters the shift converter where iron or chromic oxide catalysts, at about 425° C., further react the gas to hydrogen and carbon dioxide. Cooling then to about 38° C. is followed by $CO_2$ absorption with monethanol amine or use of the carbon dioxide in other chemical production such as urea. Hot carbonate solution may be used as a substitute for monoethanol amine. A methanator may be added to convert carbon dioxide to methane, which may be used in the pulse jet process or otherwise.

A gas may be synthesized according to the following equation:

$$3CH_4+2H_2O+CO_2\rightarrow 4CO+8H_2$$

The production of synthesis gas and carbon monoxide and hydrogen gas introduced into the combustion chamber 212/312 with zinc, chromium, manganese, or aluminum oxides as catalysts, with adjustments to the pulse jet process, create an environment of about 300° C. with pressure of about 250 to 300 bar and introduction of carbon monoxide and hydrogen yields methanol. Copper oxide catalysts may be used to allow use of lower temperatures (e.g., 200 to 300° C.) and pressures (e.g., 50-100 bar).

The methanol produced can be condensed and purified by distillation (e.g., about 65° C.). Unreacted synthesis gas is recycled. Other products may include, but are not limited to, ethanol and other higher boiling alcohols and dimethyl ether.

Methanal (formaldehyde) may be produced from methanol. The high pressure of the pulse jet system may be adjusted to produce at least heat (the chemical process is exothermic during oxidation, but endothermic during dehydrogenation). Both phases require high pressure and proceed according to the following equations:

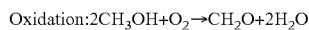

Oxidation: $2CH_3OH+O_2 \rightarrow CH_2O+2H_2O$

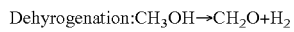

Dehyrogenation: $CH_3OH \rightarrow CH_2O+H_2$

The use of an aluminum combustion chamber 212/312, or placement of aluminum in other configuration(s) within the combustion chamber 212/312, if excess oxygen is available, allows production of aluminum oxide. In this way, similar to the production of magnetite during nitrogen fixation in an iron chamber, the process can produce its own catalyst.

Methanol is the basis for other chemical production including MTBE, acetic acid, solvents, chloromethanes, methylmethacrylate, methylamines, dimethyl terephthalate, acetic anhydride, hexamethylinediamin, isobutene, 1-butane, maleic anhydride, methyl ethyl ketone, 1-4 butanediol, butyl acrylate, n-butyl alcohol, chloroform, 2-ethylhexanol, hydrogen cyanide, methyl chloride, methylene diphenyl diisocyanide, phosgene, and toluene diisocyanate.

FIG. 4 shows another example configuration of the pulse jet system 400 for water desalination. Briefly, heated water may be introduced via inlet 401 to an evaporation chamber 402. The evaporation chamber may be a solar chamber heated by the sun. In an example, the evaporation chamber may float on a saline or otherwise polluted water source. Vapor may be evaporated in the evaporation chamber without increasing pressure. For example, the source water (water to be treated) may be heated using heated water from the exhaust of the combustion chamber 410 (e.g., as illustrated by return piping 404). The vapor moves through piping 403 through a combustion chamber 410 of the pulse jet system 400. The combustion chamber 410 has already been described above for various embodiments and therefore a detailed discussion of the combustion chamber 410 is not repeated here. The vapor exits the combustion chamber 410 under pressure and is moved by air or other gas flow through piping 411 to an expansion chamber 412, where purified water is recovered or collected via outlet 414. Exhaust from the expansion chamber may also be used to drive a turbine, for additional energy recovery.

In an example, air carrying water vapor is introduced under pressure into the gaseous exhaust of the combustion chamber 410 of the pulse jet system 400 (e.g., under the same pressure). The combination expands into a containment chamber (chamber 402) under ambient air pressure, and in so doing, cools and condenses the vapor to a potable liquid using diabetic and adiabatic cooling.

In an example, the pulse jet system 400 and method may be implemented in a 4 cycle internal combustion engine, modified as described herein, for production of purified and/or desalinated water using pressurized gas exhausted from the pulse jet process, or other pressurized gas. This gas intermixed with ambient air (which includes water vapor produced by solar, or other heat evaporating impure water) in an enclosed chamber under ambient pressure. This air is compressed to the pressure of the pulse jet exhaust and the two streams conjoined and then allowed to expand in a separate chamber back to ambient pressure. This causes condensation of the now purified/desalinated vapor to a liquid state. The process uses adiabatic and diabetic cooling to achieve condensation and by using the energy of the already pressurized exhaust gas of the pulse jet system, maximally utilizes the energy of the entire system. Lower energy heat recovered from the process can be admitted to the evaporation chamber, increasing the evaporation rate and adding to the solar energy used. In expanding, the combined gases may power a turbine to recover electrical energy to power, the compressor and any pumps, or other devices required by the system. The relatively low heat energy can also be partially recovered by using, it to power a Rankine cycle engine or generator.

In another example, the pulse jet system and method may be implemented for production of purified and/or desalinated water using gas produced from the process and under pressure to intermix the water vapor from evaporation (not steam) and recondense diabatically and adiabatically on expansion into the condensation chamber.

The pulse jet system uses pure water as vapor or mist to modulate its combustion process. The process does emit cooled gas under pressure. The pressure of the exhaust may be varied, but in most applications, a back pressure is maintained in the system to aid the process. Therefore, gas under pressure remains after end of the liquids and dissolved gases produced are removed, and the gas contains energy that may be used as follows. First, to power a turbine to produce electrical energy useful to power the pump and compressors bringing and removing combustant and substrates to and from the system. And second, the gas under pressure can be mixed with evaporated water provided by relatively low temperature heat produced by the system and which would otherwise be wasted.

The process specifically excludes steam use, defined herein as bringing water to a boil and producing steam which carries water and can also, if entrapped, produce pressure useful in a system using and producing a higher level of heat energy in purifying water. In the pulsejet system, water is evaporated (not boiled) and the energy for this includes low temperature heat energy produced by and inherent to the system which can be added by solar or concentrated solar energy, and used to augment evaporation under conditions of standard (ambient) pressure.

The process continues into a pipe carrying the gaseous exhaust of the pulse jet process, evaporated water in ambient air is compressed to substantially match the pressure of the exhaust. Then, the combined water vapor and exhaust vents and expands into a less-pressurized cooling chamber. This chamber is cooled adiabatically by expansion of the pressurized mixture, and condenses to produce salt mineral and pollutant free water which is collected and used for providing pure water to the pulse jet itself. Excess can be used for the standard uses of purified water (e.g., drinking), and the polluted and/or saline water that is evaporated may augment the cooling and condensing process when allowed to further cool the condensing vessel.

The method of purifying water also may be used apart from the pulse jet process, e.g., when a stream of gas under pressure is produced in any way wherein steam formation is avoided, and this gas intermixed with ambient air containing water vapor via the process of evaporation. The mixture is cooled an condensed by the cooling and condensing effect of the expansion of the gas with or without the addition of diabetic cooling through contact with cool air or water.

It is noted that when the pulse jet system is used for water production, the cooled gas under pressure may be exhausted after all combustion and chemical reactions are completed, and may be expanded directly into a larger chamber which exhausts to the ambient atmosphere. This provides cooling by adiabatic expansion and can be used for refrigeration and air conditioning.

Having described various example systems, processes, operations, and applications and examples thereof, reference will now be made to further actual use examples based on laboratory experiments. It is noted that these examples are provided only for the purpose of illustrating to one having ordinary skill in the art how to practice the invention, but are not intended to be limiting in any manner.

In an actual use example, the combustion chamber was configured as a cylinder substantially as shown schematically in FIG. 1. The cylinder used for the combustion chamber had a diameter of about 5.0 centimeters (cm) and a volume of about 4,000 milliliters (mL). The diameter of the cylinder tapered at about 50% of the length of the cylinder at a slope of about 1:2. The nozzle between the combustion chamber and the expansion chamber had a diameter of about 1.0 cm. The expansion chamber was also configured as a cylinder substantially as shown schematically in FIG. 1. The cylinder used for the expansion chamber had a diameter of about 5.0 centimeters (cm) and a volume of about 10,000 mL. The expansion chamber included water vapor cooling, injected at a flow rate of about 10.0 g for each explosive cycle. A constant flow of ambient air (comprising approximately 80% $N_2$ gas and 20% $O_2$ gas) was introduced at a flow rate of about 50 mL/sec into the combustion chamber along with a ratio of 1,000 mL of pure $O_2$ gas for every 250 mL of pure $H_2$ gas. The gas mixture was ignited by spark.

The measured temperature and pressure of the explosion varied based on the ratios of the gas mixture, and also with the amount of water vapor admitted with the ambient air. In one example, the temperature at the nozzle was measured at about 2200° C. and the pressure was measured at about 7.0 bar. These parameters can be readily varied and controlled using standard laboratory techniques to produce the desired yield. Again, the critical temperatures and pressures are within the limited area of explosion and vary widely with the water vapor included with the admitted gases.

Yields of ammonia, ammonium nitrate and nitric acid also varied based on the operating parameters. Examples yields based on the above parameters were measured at 0.11 grams of ammonium nitrate per 1.000 hydrogen when operated in the ammonium nitrate producing mode (compare to about 0.33 grams using the Haber process). Example yields were measured at 0.26 grams of ammonia per liter of hydrogen when operated in the ammonia producing mode (compare to about 0.33 grams using the Haber process). The yields are also influenced by inefficiencies of the process itself. Examples include the one way valves, which allow product to escape prior to full closure and may not necessarily seal fully. The valves can be further improved to reduce or eliminate these effects. Another inefficiency is from NO not leaving the chamber to form $HNO_3$ before reverting to $N_2$ and $O_2$.

Although yields were somewhat lower than those expected using the Haber process, the operations disclosed herein are less energy intensive. That is, the process can be accomplished without the need for carbon-based energy or feedstock. In addition, the operations can be carried out on a smaller scale, in remote environments without the need for elaborate laboratory establishments and/or expensive, difficult to operate equipment.

It is noted that while specific parameters are given for the above examples, all sizing, temperatures, pressures, and gas flow rates can be adjusted based on various design considerations and to achieve the desired yields.

The examples shown and described herein are provided for purposes of illustration and are not intended to be limiting. Still other examples are also contemplated.

The invention claimed is:

1. A method of water desalination and purification, comprising:
    introducing heated water to an evaporation chamber, wherein vapor is evaporated without increasing pressure;
    moving the vapor into exhaust of a pulse jet; and
    exiting the vapor in air, and the exhaust of the pulse jet, under pressure to an expansion chamber to produce purified water.

2. The method of claim 1, further comprising recovering energy in the expansion chamber.

3. The method of claim 1: further comprising pumping water into the evaporation chamber.

4. The method of claim 1, further comprising solar heating the heated water in the evaporation chamber.

5. The method of claim 1, further comprising removing pure water from the expansion chamber.

\* \* \* \* \*